US011802262B2

(12) United States Patent
Yu et al.

(10) Patent No.: US 11,802,262 B2
(45) Date of Patent: Oct. 31, 2023

(54) METHOD AND SYSTEM FOR ACCELERATING FOOD OXIDATION RATE

(71) Applicant: Millitronic Co., Ltd., New Taipei (TW)

(72) Inventors: Ya-Chung Yu, New Taipei (TW); Chih-Min Lin, New Taipei (TW)

(73) Assignee: Millitronic Co., Ltd., New Taipei (TW)

( * ) Notice: Subject to any disclaimer, the term of this patent is extended or adjusted under 35 U.S.C. 154(b) by 347 days.

(21) Appl. No.: 17/257,862

(22) PCT Filed: Jul. 6, 2018

(86) PCT No.: PCT/CN2018/094893
§ 371 (c)(1),
(2) Date: Jan. 5, 2021

(87) PCT Pub. No.: WO2020/006760
PCT Pub. Date: Jan. 9, 2020

(65) Prior Publication Data
US 2021/0292691 A1    Sep. 23, 2021

(51) Int. Cl.
*C12H 1/16* (2006.01)
*A61L 2/025* (2006.01)
*H05B 6/00* (2006.01)

(52) U.S. Cl.
CPC .............. *C12H 1/165* (2013.01); *A61L 2/025* (2013.01); *H05B 6/00* (2013.01)

(58) Field of Classification Search
CPC ... C12H 1/00; C12H 1/06; C12H 1/14; C12H 1/16; C12H 1/165; C12H 1/18;
(Continued)

(56) References Cited

U.S. PATENT DOCUMENTS

| 7,361,255 B1* | 4/2008 | Kuhry | A23L 2/50 |
| | | | 204/164 |
| 2006/0155855 A1 | 7/2006 | Hamai | |

(Continued)

FOREIGN PATENT DOCUMENTS

| CN | 1385516 A | 12/2002 |
| CN | 1548521 A | 11/2004 |

(Continued)

OTHER PUBLICATIONS

"International Search Report" dated Apr. 3, 2019 for International application No. PCT/CN2018/094893, International filing date:Jul. 6, 2018.

*Primary Examiner* — Hung D Nguyen
(74) *Attorney, Agent, or Firm* — Winston Hsu

(57) ABSTRACT

The present invention provides a system for accelerating the food oxidation rate, comprising a control unit, a baseband circuit, a radio-frequency circuit and an array of antennas. The control unit is used to generate a digital control signal of a spectrum waveform. The baseband and radio-frequency circuits generate analog signal of millimeter-wave according to the control signal of a spectrum waveform. The baseband circuit and the array of antennas emit the analog signal of millimeter-wave toward the food, wherein the analog signal of millimeter-wave has a plurality of first frequency signals and a plurality of second frequency signals, and the first frequency signals and the second frequency signals are alternately arranged and spaced from each other and comprise a plurality of sinusoidal waveforms.

12 Claims, 8 Drawing Sheets

(58) Field of Classification Search
CPC ... C12H 1/22; H05B 6/00; H05B 6/46; H05B 6/62; H05B 1/40; H05B 1/50; A61L 2/02; A61L 2/025
See application file for complete search history.

(56) References Cited

U.S. PATENT DOCUMENTS

| | | |
|---|---|---|
| 2007/0243556 A1 | 10/2007 | Wachs |
| 2010/0303178 A1 | 12/2010 | Sorrells |
| 2014/0141120 A1 | 5/2014 | Ugliano |
| 2016/0256703 A1* | 9/2016 | Schwarz ............... A61N 5/022 |
| 2018/0168727 A1 | 6/2018 | Lin |

FOREIGN PATENT DOCUMENTS

| | | |
|---|---|---|
| CN | 101001944 A | 7/2007 |
| CN | 101525572 A | 9/2009 |
| CN | 203144380 U | 8/2013 |
| CN | 104884950 A | 9/2015 |
| CN | 205205118 U | 5/2016 |
| CN | 108070509 A | 5/2018 |
| KR | 10-0835309 B1 | 6/2008 |
| TW | 201328015 A1 | 7/2013 |
| TW | 201816104 A | 5/2018 |

\* cited by examiner

METHOD AND SYSTEM FOR ACCELERATING FOOD OXIDATION RATE

BACKGROUND OF THE INVENTION

1. Field of the Invention

The present invention relates to a system and method for accelerating the oxidation rate of food, and more particularly, to a system and method for accelerating the oxidation rate of food by using millimeter-wave signals.

2. Description of the Prior Art

Polyphenols are commonly found in plants (such as vegetables and fruits). Among them, most of the "polyphenols" are powerful metal ion chelators, so they are able to be combined with free ferric ion or ferrous ion in cells, thereby reducing the number of reactive oxygen species generated by Fenton reaction or Haber-Weiss reaction; secondly, polyphenols are also scavengers for superoxide anion radicals and hydroxyl radicals. Both superoxide anion radicals and hydroxyl radicals could cause lipid peroxidation reaction; finally, polyphenolic compounds could react with peroxy radicals to terminate the lipid peroxidation chain reaction. Thus, it could be understood that polyphenolic compounds are actually a good natural antioxidant, which could be used to reduce the production of reactive oxygen species and effectively scavenge free radicals so as to prevent brain and cardiovascular diseases, diabetes, kidney diseases, and so forth.

There are already polyphenolic compounds in various kinds of foods. For example, red wine contains: Tannins, Anthocyanidin, Resveratrol, etc., which are not only favored by people, but also for people pursuing health and used to have a drink before going to bed. However, because polyphenolic compounds can affect the color and taste of red wine, people usually decants the red wine before tasting it. The decanting process could not only enhance the aroma of the red wine, but also make the taste of the red wine soft, round and smooth. Generally speaking, so-called "decanting" is to let the wine contact the air, through which the polyphenolic compounds could be oxidized by the oxygen molecules of the air and thereby change the taste of red wine. However, a conventional method for decanting red wine usually includes the processes of filling a decanter with red wine and leaving the filled decanter to stand for several hours so as to allow the red wine in the decanter to be oxidized by the air. However, the aforementioned decanting time is obviously too long. Thus, most people will go on to deal with other things during the decanting process and forget that the red wine is in the decanting process, which leading to over oxidation of the red wine. At this time, the aroma and taste of the red wine will gradually deteriorate, and even cause the red wine to be too bitter to drink, thereby making people feel bad drinking experience, ruining people's original pleasant mood, and failing to meet people's expectation.

Therefore, due to the long waiting time of the conventional decanting method, users who are distracted to deal with other matters will often miss the best time for drinking the red wine. Therefore, how to solve the aforementioned problems effectively is the purpose of the present invention.

SUMMARY OF THE INVENTION

In view of the fact that the conventional decanting method are still not perfect, after many years of practical experience and after many experiments and researches, the inventor has designed a system for accelerating the oxidation rate of polyphenolic compounds in food and a method thereof in order to meet market demand.

According to one embodiment of the present invention, the present invention provides a system for accelerating the food oxidation rate, comprising a control unit, a baseband circuit, a radio-frequency circuit and an array of antennas. The control unit is used to generate a digital control signal of a spectrum waveform. The baseband and radio-frequency circuits generate analog signal of millimeter-wave according to the control signal of a spectrum waveform. The baseband circuit and the array of antennas emit the analog signal of millimeter-wave toward the food, where the analog signal of millimeter-wave has a plurality of first frequency signals and a plurality of second frequency signals, and the first frequency signals and the second frequency signals are alternately arranged and spaced from each other and comprise a plurality of sinusoidal waveforms.

According to another embodiment of the present invention, the present invention provides a method for accelerating the oxidation rate of food. Food is provided first, and then analog signal of millimeter-wave is transmitted to the food, where the analog signal of millimeter-wave includes a plurality of first frequency signals and a plurality of second frequency signals, and the first frequency signals and the second frequency signals are alternately arranged and each includes a plurality of sinusoidal waveforms.

With the system and method provided in the present invention, the system and method of the present invention could further shorten the waiting time necessary for the conventional decanting process.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
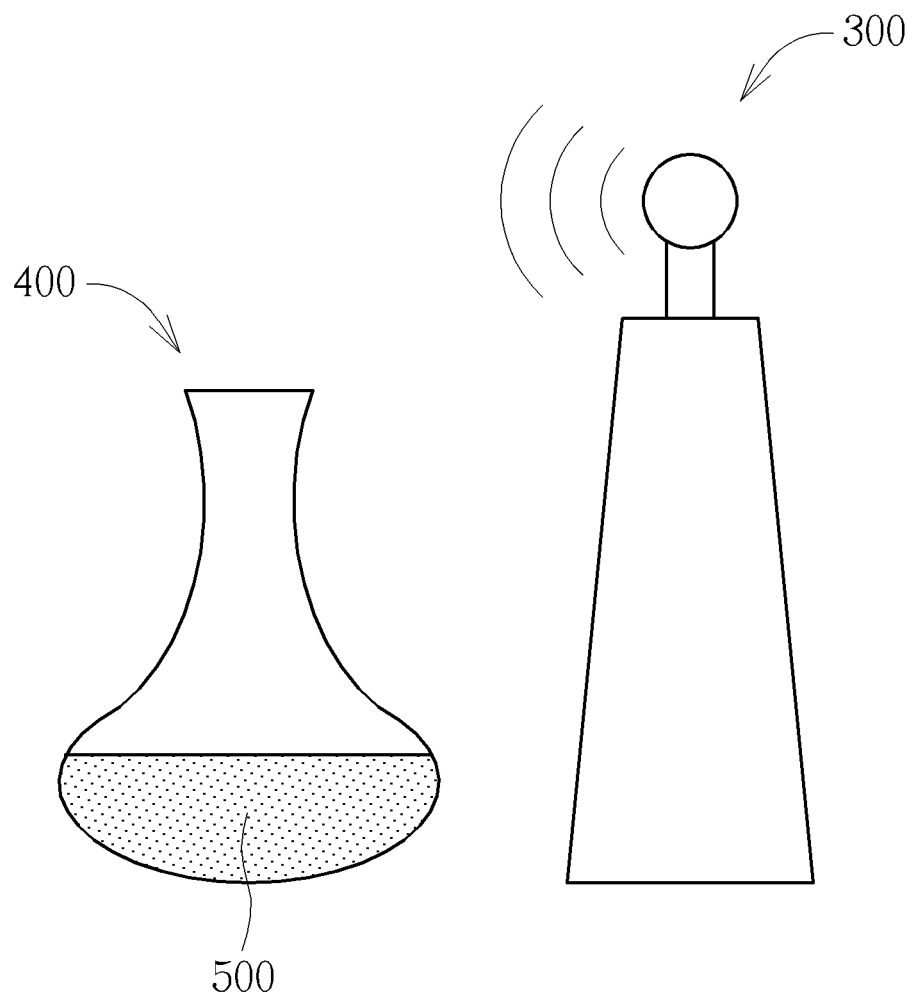
FIG. 1 is a schematic diagram of a system for accelerating the oxidation rate of food according to one embodiment of the present invention.

The invention provides a system for accelerating the oxidation rate of food. Referring to FIG. 1, FIG. 1 is a schematic diagram of a system for accelerating food according to one embodiment of the present invention. As shown in FIG. 1, the system 300 is designed for food 500 in a container 400. According to one embodiment, the food 500 may be any product and its raw materials, the flavor and taste of which may be increased through an oxidation reaction and which may be edible or chewable for human. It may be solid, liquid, or even gaseous. According to one embodiment of the present invention, the food 500 refers to a food that requires a yeast-containing fermentation process, such as yogurt, cheese, sweet fermented rice, pickles, soy sauce, vinegar, tempeh, rice wine, beer, wine, and so forth, but not limited thereto. According to a preferred embodiment of the present invention, the food is a fermented food and a drink containing polyphenolic compounds, such as Catechin, Chlorogenic acid, Isoflavones, anthocyanidin, cocoa polyphenols, curcumin, Hesperidin, quercetin, rutin, resveratrol, and so forth, but not limited thereto. According to a preferred embodiment, the food 500 is red wine containing polyphenolic compounds. The polyphenolic compounds include phenolic acid, flavonoid compounds, such as Tannins, Anthocyanidin, and non-flavonoid compounds, such as Resveratrol, and so forth. According to another embodiment of the present invention, the food 500 is yogurt or yogurt.

The container 400 may be any device with a containing function, such as a bottle or a cup and so forth with various shapes. The container 400 has a space for placing the food 500. The material of the container 400 is not limited, but at least a part of the container 400 may allow electromagnetic waves to pass through according to one embodiment. The material of this part may be, for example, glass, plastic, and so forth, but not limited thereto. Preferably, the part which allows the electromagnetic wave to pass through is close to the interface between the air and the food. Preferably, the container 400 does not contain metal.

Figure 2:
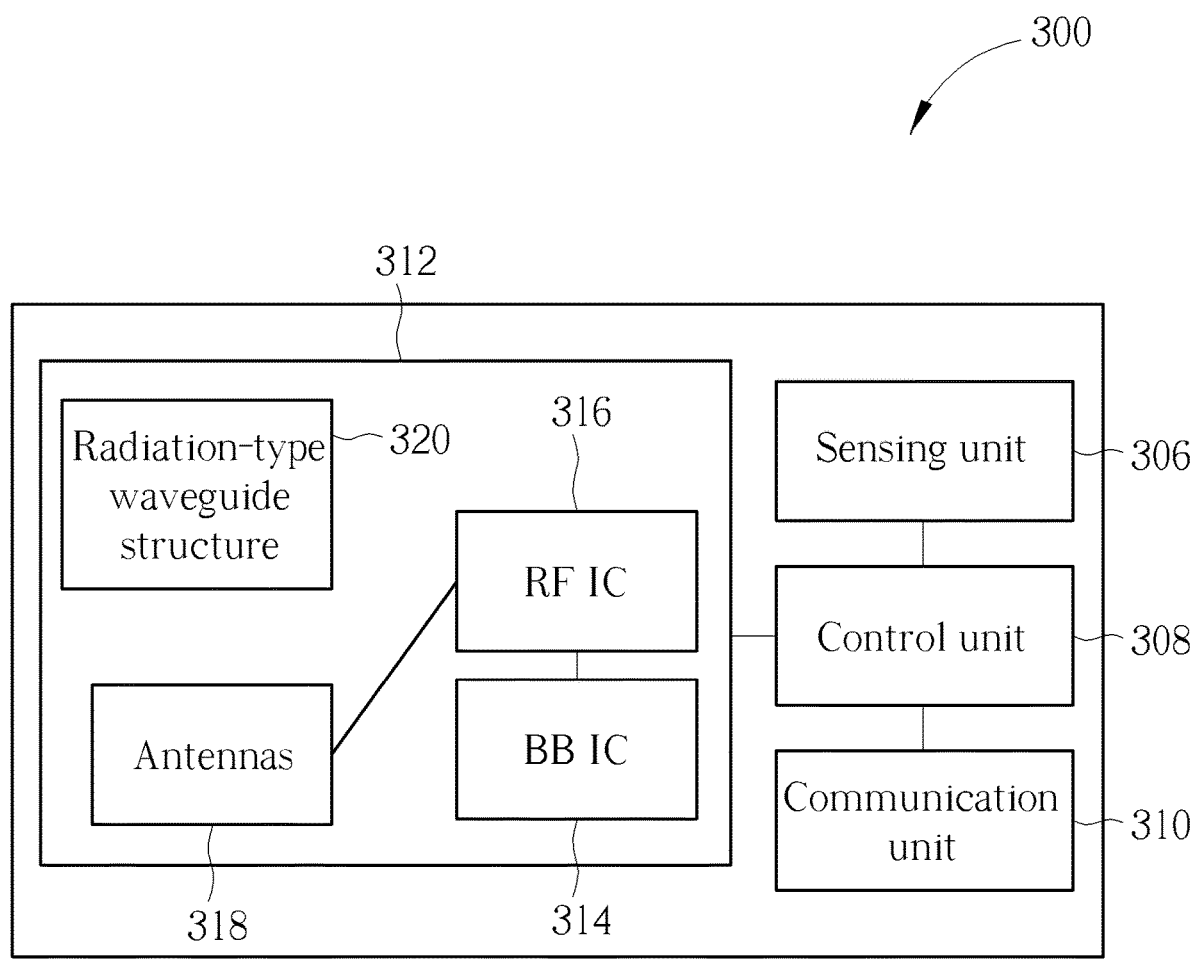
FIG. 2 is a block diagram of a system for accelerating the oxidation rate of food according to the present invention.

Referring to FIG. 2, FIG. 2 is a block diagram of a system for accelerating the oxidation rate of food according to the present invention. As shown in FIG. 2, the system 300 includes a sensing unit 306, a processing unit 308 and an oxidation device 312. The sensing unit 306 generates a sensing signal used to indicate the oxidation state of the food. According to one embodiment, the sensing unit is, for example, gas analysis equipment, which may determine the components (such as alcohol concentration) of the air above the food 500 by analyzing absorption spectrum, so as to obtain the oxidation state of the food 500. According to the present embodiment, a sensing device may include a signal emitting terminal (not shown), a reflective device (not shown), and a signal receiving terminal (not shown). The signal emitting terminal is used to emit light through the air above the food 500, and the light is received by the signal receiving terminal after being reflected by the reflective device, thereby generating the sensing signal.

The control unit 308 is coupled to the sensing unit 302 and may receive the sensing signal. The control unit 308 may find the corresponding digital signal of the spectrum waveform in the database according to the sensing signal. The database is an integrated database that stores various spectrum waveform signals suitable for different foods (e.g., fermented foods) in different oxidation states. The database may be set in a storage unit (not shown) in the system 300. According to one embodiment, data from the database of the storage unit may be updated online with other databases through the communication unit 310 at any time. The communication unit 310 may be any devices or components with communication functions, such as Near Field Communication (NFC), Bluetooth, Wired/Wireless Area Network (LAN), Storage Area Network (SAN), Internet, and so forth but not limited thereto. According to one embodiment, the communication unit 310 is a Bluetooth communication unit, and the Bluetooth communication unit may be connected to a personal computer or a handheld mobile device to update the database.

Figure 3:
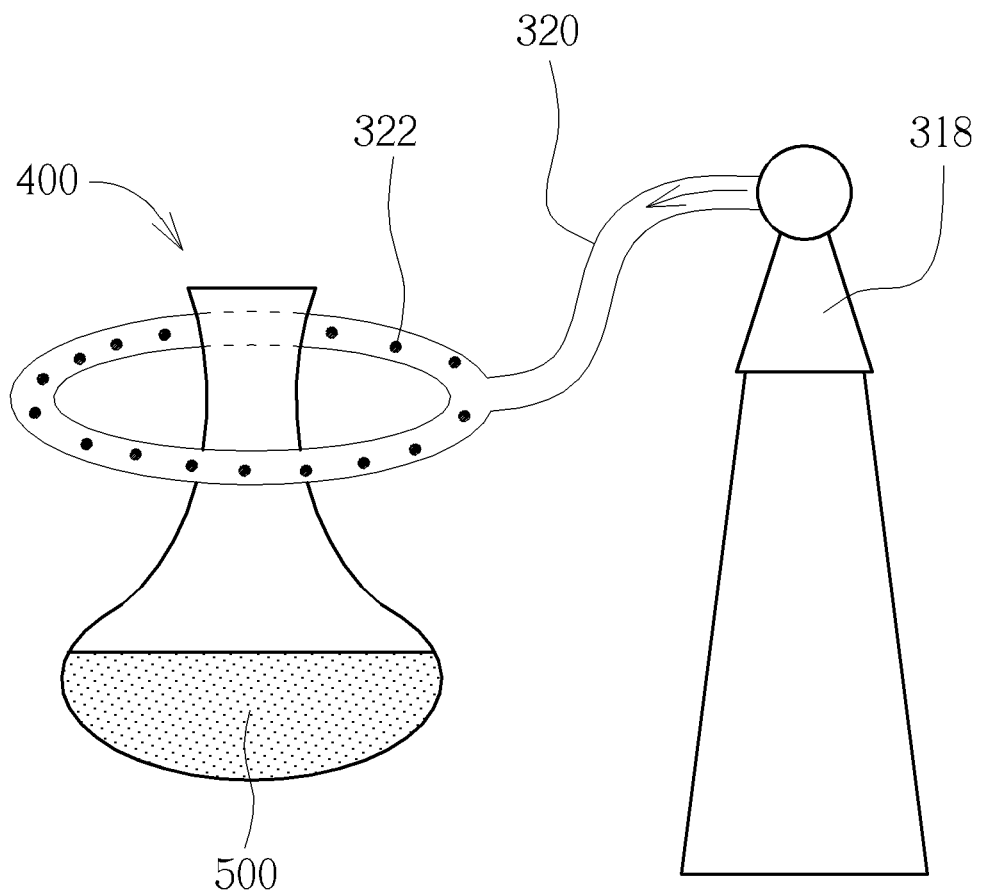
FIG. 3 is a schematic diagram of an array of antennas according to the present invention.
Figure 4:
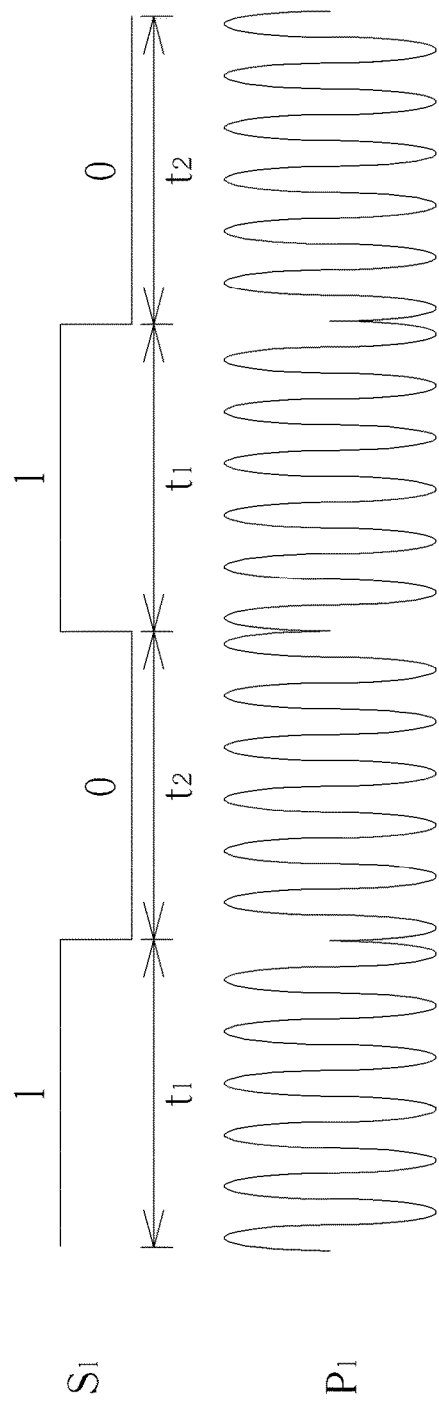
FIG. 4 to FIG. 7 are schematic diagrams of the waveform of the radiation of millimeter-wave according to the present invention.
Figure 5:
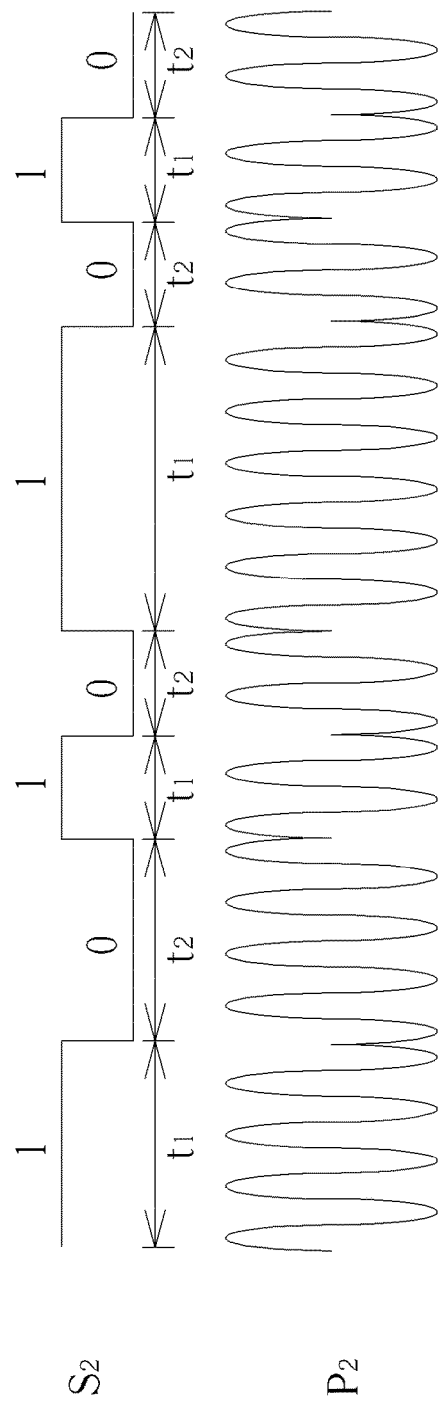
Figure 6:
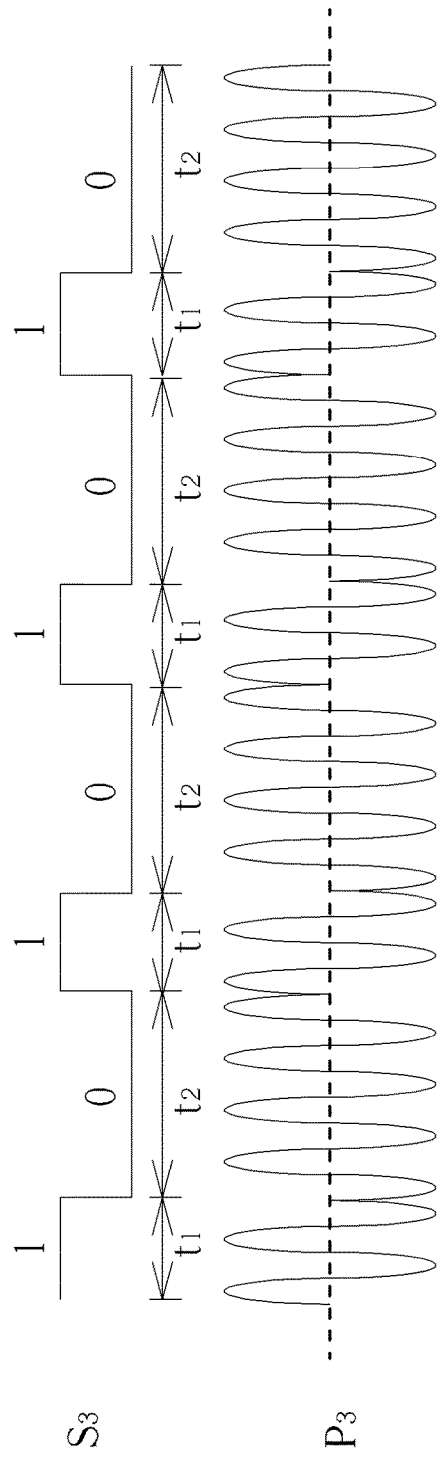
Figure 7:
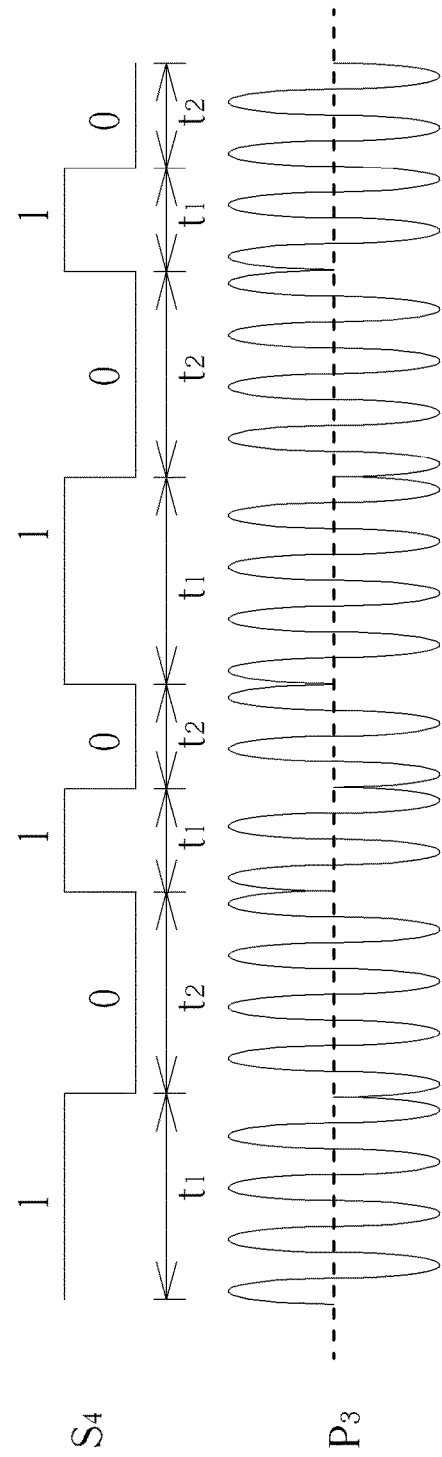

Next, still referring to FIG. 2, the control unit 308 transmits the corresponding digital signal of the spectrum waveform to the baseband circuit 314 of the oxidation device 312, and the baseband circuit 314 may generate analog signals with various corresponding waveforms, frequency, and amplitude or time domain according to the received digital signals of spectrum waveform. Then, the radio frequency unit 316 of the oxidation device 312 converts this analog signal into a millimeter-wave signal with a frequency between 56 GHz and 65 GHz. Then, the millimeter-wave signal is emitted by an array of antennas 318 to irradiate the target required to be oxidized (i.e., the food 400), so that the target may undergo a millimeter-wave related accelerated oxidation reaction. According to one embodiment, referring to FIG. 3, FIG. 3 is a schematic diagram of an array of antennas of the present invention. According to this embodiment, the array of antennas 318 may further include a radiation-type waveguide structure 320, which refers to a ring-shaped structure with a plurality of openings 322, so that the generated millimeter-wave may surround the target required to be oxidized and provide millimeter-wave radiation.

The principle of using millimeter-waves to accelerate the oxidation rate of food in the present invention is as follows: by using red wine as an example, the red wine and the air adjacent to the liquid surface form an electromagnetic field due to the oscillation of millimeter-wave, and the electromagnetic wave signal may continuously activate the oxygen molecules in the air adjacent to the liquid surface of the red wine to thereby form more superoxide anions ($O_2$—) and singlet oxygen molecules ($1O_2$). At this time, for the polyphenolic compounds adjacent to the liquid surface, the hydrogen atoms and the electrons in the hydroxyl groups (—OH) may be promptly captured by singlet oxygen molecules ($1O_2$) so that the activated singlet oxygen molecules ($1O_2$) may be converted to triplet oxygen molecules and produce water ($H_2O$) concurrently; the hydrogen atoms in the hydroxyl groups (—OH) may also be promptly captured by the superoxide anion ($O_2$—) and thereby produce extremely active hydrogen superoxide ($HO_2$) and produce water ($H_2O$) in a chain reaction. The polyphenols may be oxidized into phenates.

One feature of the present invention is that millimeter-wave radiation with special waveforms is provided to accelerate the oxidation reaction in the food. According to a preferred embodiment of the present invention, the analog signal of millimeter-wave comes from a digital signal of spectrum waveform stored in a database, and the data in the database may correspond to each parameter of each kind of product. Taking red wine as an example, the database may contain data of corresponding digital signals with spectrum waveform, and the data may be established based on the type, year, and place of origin of red wine. According to this embodiment, the system 300 may also have an identification unit (not shown), which is able to scan and identify the product label on the red wine bottle. By using the identification unit and the sensing signal, more accurate red wine data may be obtained so as to generate optimized millimeter-wave analog signals and to get the most suitable (or user-defined favorite) taste.

In the aforementioned database, there are already a number of established digital signals corresponding to millimeter-wave signals with required waveforms, and the digital signals may, for example, be converted into millimeter-wave analog signals during decanting. The invention provides several forms of millimeter-wave analog signals, which are proven to effectively accelerate the oxidation rate of food. The millimeter-wave analog signal of the present invention has a plurality of first frequency signals and a plurality of second frequency signals, the first frequency signal and the second frequency signal are alternately arranged, and the first frequency signal and the second frequency signal include a plurality of sinusoidal waveforms. The phase, amplitude, and duration of these sinusoidal waveforms may vary according to different foods. However, preferably, the first frequency signal and the second frequency signal have opposite phases. In another embodiment, the first frequency signal and the second frequency signal have the same frequency and amplitude.

Please refer to FIG. 4 to FIG. 7. FIG. 4 to FIG. 7 are schematic diagrams of the millimeter-wave radiation of the present invention. As shown in FIG. 4 to FIG. 7, the waveforms P1~P4 are all sinusoidal functions, the first frequency signal (indicating by the reference numeral "1", lasting a period of time $t_1$) and the second frequency signal (indicating by the reference numeral "2", lasting a period of time $t_2$) has the same frequency and amplitude, and the first frequency signal and the second frequency signal have opposite phases, that is, the first frequency signal starts at a positive phase and ends at a negative phase; and the second frequency signal starts at a negative phase and ends at a positive phase. In an embodiment, different millimeter-wave radiation is formed by controlling the first period of time $t_1$ of the first frequency signal and the second period of time $t_2$ of the second frequency signal. For FIG. 4, the first period of time $t_1$ of the first frequency signal is the same as the second period of time $t_2$ of the second frequency signal; in FIG. 5, the first period of time $t_1$ is greater than or equal to the second period of time $t_2$; in FIG. 6, the first period of time $t_1$ is ½ of the second period of time $t_2$; in FIG. 7, the difference between each first period of time $t_1$ and the immediate next first time $t_1$ is a fixed value, and the difference between each second period of time $t_2$ and the immediate next second time $t_2$ is a fixed value. According to the embodiments above, the number sequence presented at each first period of time $t_1$ and second period of time $t_2$ may be presented in a meaningful way, or each group of the first period of time $t_1$ and second period of time $t_2$ may also be presented in a meaningful way. Of course, according to the abovementioned embodiments, the amplitude and frequency of the first frequency signal is fixed, but the first period of time $t_1$ and the second period of time $t_2$ are changed to generate different millimeter-wave radiation signals. According to some embodiments, the first period of time $t_1$ and the second period of time $t_2$ may be fixed, but the frequency of the first frequency signal (first frequency) and the frequency of the second frequency signal (second frequency) are changed to generate different millimeter-wave radiation signals. According to some embodiments, two or three of the factors such as frequency, time period and amplitude may be changed in order to generate different millimeter-wave radiation signals.

In another embodiment of the present invention, the control unit 308 can also calculate the signal of spectrum waveform in real time (in-situ) using the sensing signal from the sensing unit 306 according to the oxidation degree of the food, and then the baseband circuit 314 in the oxidation device 312 may generate a millimeter-wave analog signal. The millimeter-wave analog signal may then be transmitted to the food 500 by the radio frequency circuit 316. At this time, the sensing unit 306 may be set to synchronously update the oxidation degree of the food 500 at regular intervals (for example, every 5 seconds), so the generated millimeter-wave analog signal may also be updated at intervals in order to match the state of the food 500 and to acquire the desired oxidation effect. In another embodiment of the present invention, the sensing unit 306 may sense several substances to generate multiple sets of sensing signals, and the control unit 308 may generate multiple signals of spectrum waveforms based on the multiple sets of sensing signals. The baseband circuit 314 is then used to synthesize the corresponding millimeter-wave analog signals. In another embodiment, a user feedback system may also be established. The user may adjust the parameters to obtain the corresponding millimeter-wave analog signal based on the user's favorite food flavor. The signal may be uploaded or shared in the database, so that other users may use the information to let the food produce the same flavor, which promotes the processing of food to the level of "molecular gastronomy".

Figure 8:
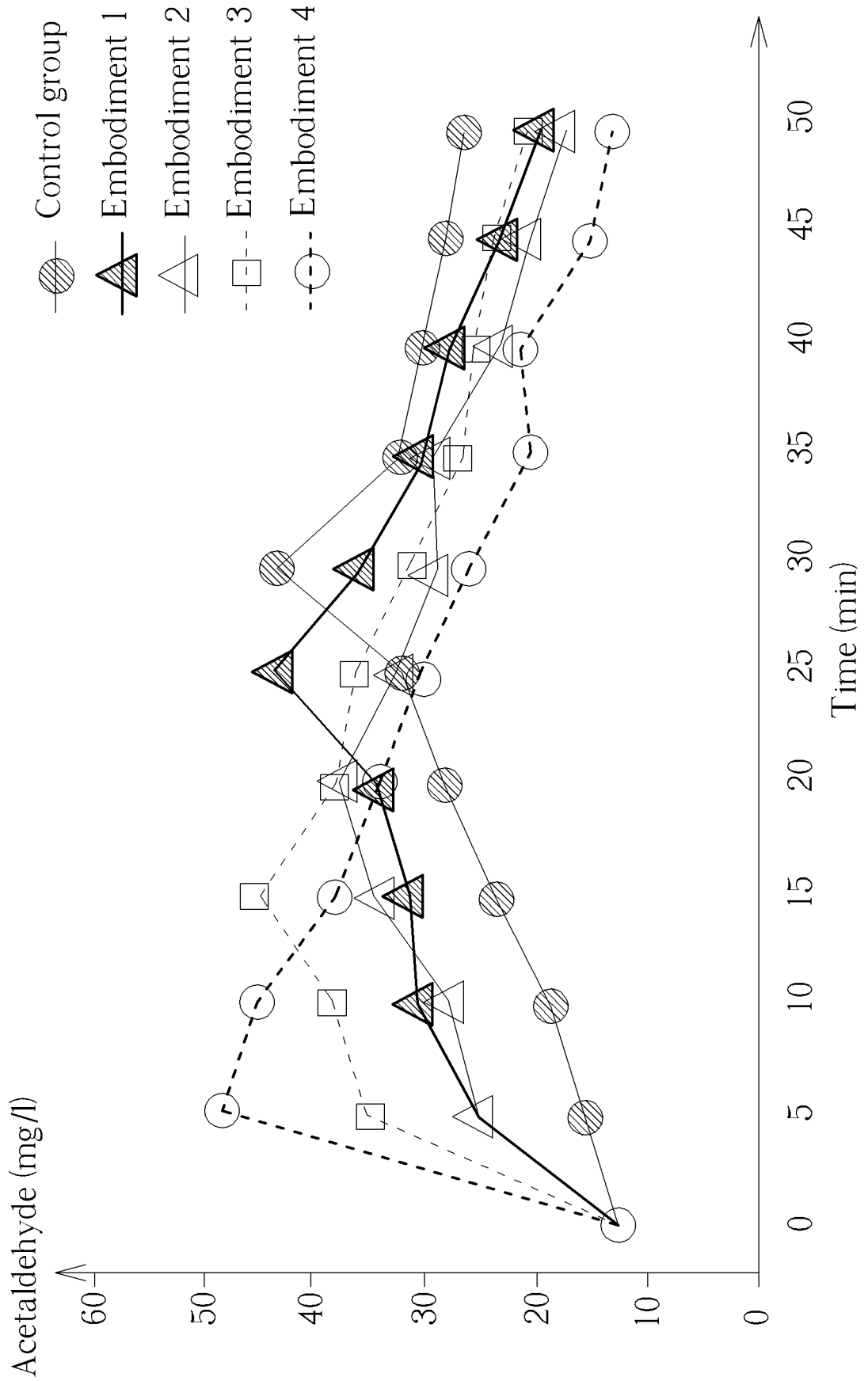
FIG. 8 is a broken line diagram of the effect of radiation signals of millimeter-wave on the oxidation rate of red wine according to different embodiments of the present invention.

Please refer to FIG. 8. FIG. 8 is a broken line diagram of the effect of radiation signals of millimeter-wave on the oxidation rate of red wine according to different embodiments of the present invention, where the horizontal axis is time (unit: minutes), and the vertical axis is the concentration of acetaldehyde (unit: mg/l) which represents the result of oxidation degree in red wine. As shown in FIG. 8, the circle with slanted lines represents the control group, the triangle with slanted lines represents the first embodiment using the waveform of FIG. 4, the open triangle represents the second embodiment using the waveform of FIG. 5, the open square represents the third embodiment using the waveform of FIG. 6, and the open circle indicates the embodiment using the waveform of FIG. 7. As shown in FIG. 8, in the control group without any millimeter-wave radiation signals, the time corresponding to the highest acetaldehyde concentration is longest, which is about half an hour (30 minutes). In different embodiments, the oxidation rate may be increased to shorten the time corresponding to the peak acetaldehyde concentration. Among all of the embodiments, the fastest one is embodiment 4, which may reach the peak acetaldehyde concentration within 5 minutes and is 6 times faster than the control group. The embodiments of the present invention prove that the millimeter-wave radiation signals of the special waveform may indeed accelerate the oxidation rate of red wine and greatly shorten the decanting time.

Figure 9:
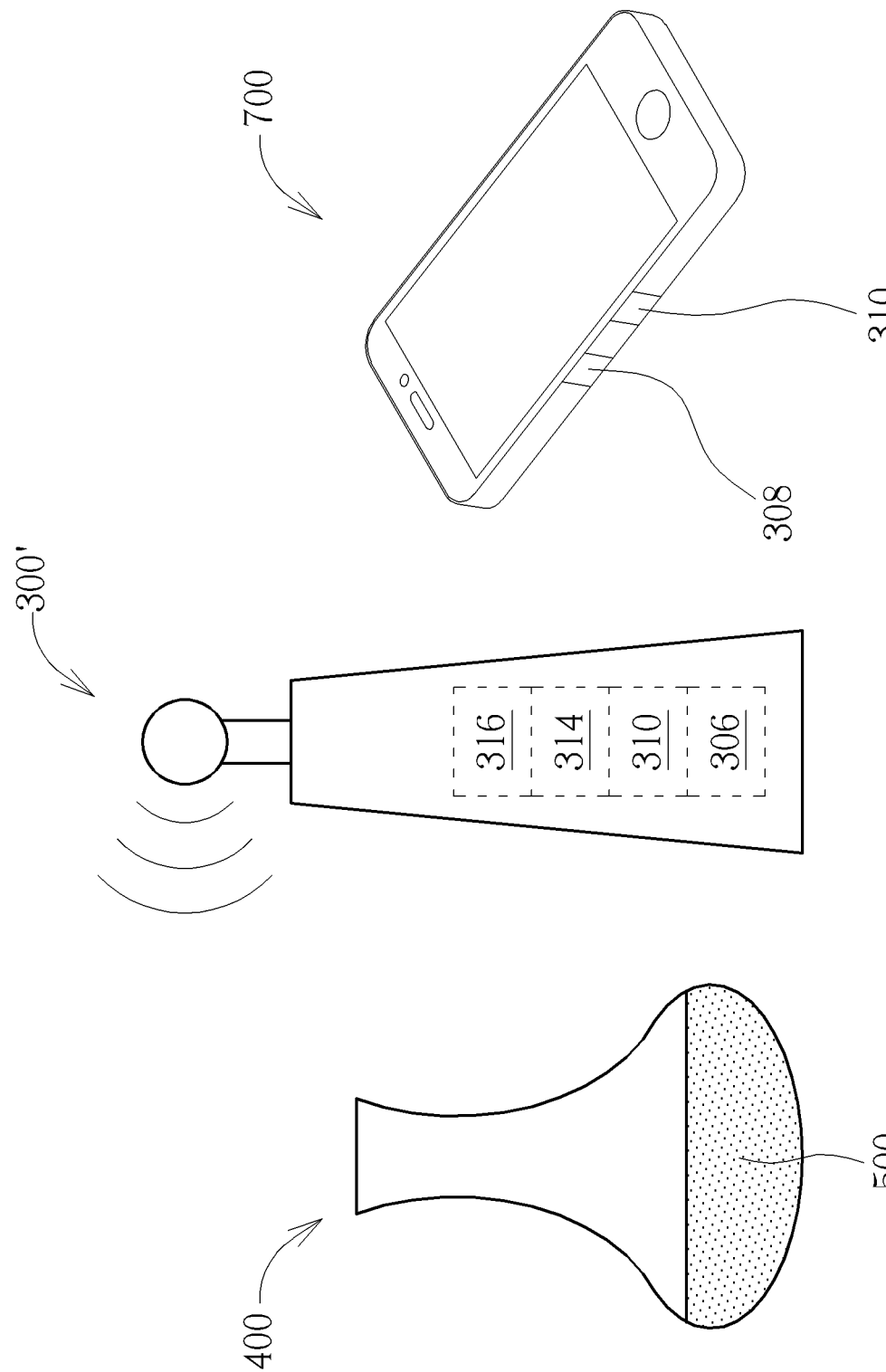
FIG. 9 is a schematic diagram of a system for accelerating the oxidation rate of food according to another embodiment of the present invention.
Figure 10:
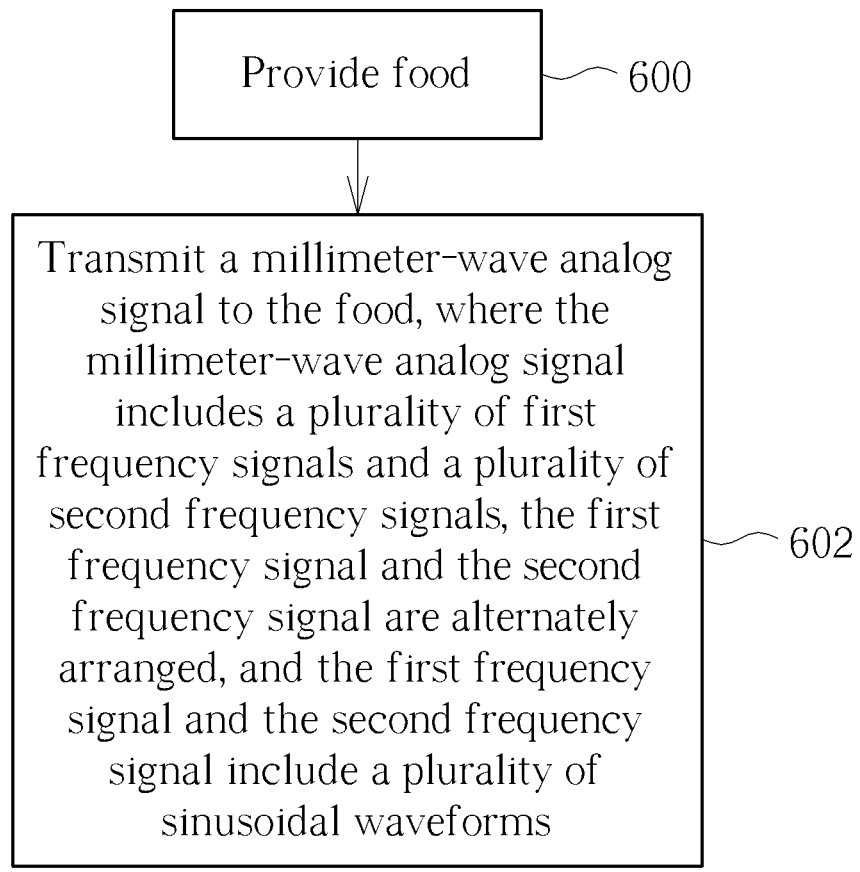
FIG. 10 is a schematic flow chart of a method for accelerating the oxidation rate of food according to the present invention.

It is worth noting that, in the system 300 for accelerating the oxidation rate of food according to the present invention, the various devices may be assembled in hardware equipment, or separately arranged and integrated into conventional electronic equipment for execution. For example, the system 300 may be integrated in hardware equipment, where the control unit 308, the communication unit 310, the radio frequency circuit 316, or the baseband circuit 314 may be packaged in the same system on chip. In order to process the food 400 individually and independently, according to one embodiment, the system 300 may be designed in a box shape to accommodate the food 500 and the container 400. Alternatively, according to another embodiment, the system 300 may be integrated in the container 400, so that the container 400 itself has the ability to accelerate oxidation process like the system 300 does. Alternatively, the system 300 may be a module which could be integrated into a conventional electronic product, such as mobile phone. Alternatively, the devices of the system 300 may be separately arranged in different hardware, for example, the radio frequency circuit 316, the baseband circuit 314, the communication unit 310, and the sensing unit 306 are integrated into a chip, which may be arranged in independent hardware. Or integrated in the container 400, and the control unit 308 may be controlled by conventional electronic equipment, such as a mobile phone. Please refer to FIG. 9. FIG. 9 is a schematic diagram of a system for accelerating the oxidation rate of food according to another embodiment of the present invention. As shown in FIG. 9, the control unit 308 according to this embodiment may be located in a handheld mobile device, such as a mobile phone 700. The user may operate the control unit 308 through the user interface UI on the mobile phone 700. According to built-in database of the application (APP) of the mobile phone, or cloud database on the network, the control unit 308 may select the appropriate digital signal of spectrum waveform. In order to generate a millimeter-wave signal, this digital signal of spectrum waveform is transmitted through the communication unit 310 to the radio frequency (RF) IC 316 and the baseband (BB) IC 314 on another hardware. Then, through the array of antennas 318, the oxidation rate of the food 500 in the container 400 may be accelerated by the millimeter-wave. Alternatively, in conjunction with conventional smart home appliances, the units in the system 300 may be connected with one another through different home appliance systems.

To summarize, the system and method for accelerating the oxidation rate of food provided by the present invention use analog signals of millimeter-wave with special waveforms, so the oxidation rate of food may be greatly increased, and the flavor of various fermented food may be added. Besides, the programmed waveform may be used to precisely adjust the desired orientation, so that the food can move towards the level of "molecular gastronomy".

The foregoing descriptions are only preferred embodiments of the present invention, and all equivalent changes and modifications made in accordance with the scope of the patent application of the present invention should fall within the scope of the present invention.

What is claimed is:

1. A system for accelerating an oxidation rate of food, comprising:
a sensing unit, configured to detect an oxidation state of the food and thereby generate a sensing signal;
a control unit, configured to retrieve a digital signal of a spectrum waveform from a database according to the sensing signal, and the control unit is configured to generate a corresponding digital signal of the spectrum waveform according to the oxidation state of the food;
a baseband circuit and a radio frequency circuit, configured to generate an analog signal of millimeter-wave according to the corresponding digital signal of the spectrum waveform; and
an array of antennas coupled with the radio frequency circuit and configured to emit the analog signal of millimeter-wave toward the food, wherein the analog signal of millimeter-wave comprises a plurality of first frequency signals and a plurality of second frequency signals, and the first frequency signals and the second frequency signals are alternately arranged, and the first and second frequency signals comprise a plurality of sinusoidal waveforms.

2. The system for accelerating the oxidation rate of the food of claim 1, wherein phases of the first frequency signals are opposite to phases of the second frequency signals.

3. The system for accelerating the oxidation rate of the food of claim 1, wherein the first frequency signals and the second frequency signals have the same frequency and amplitude.

4. The system for accelerating the oxidation rate of the food of claim 3, wherein the first frequency signals are maintained for a first period of time and the second frequency signals are maintained for a second period of time.

5. The system for accelerating the oxidation rate of the food of claim 4, wherein each first period of time is equal to each second period of time.

6. The system for accelerating food oxidation rate of claim 4, wherein each first period of time is ½ of each second period of time.

7. The system for accelerating food oxidation rate of claim 4, wherein a difference between each first period of time and an immediate next first period of time is a fixed value, and a difference between each second period of time and an immediate next second period of time is a fixed value.

8. The system for accelerating food oxidation rate of claim 1, further comprising a communication unit, wherein the control unit is connected to the database through the communication unit.

9. The system for accelerating the oxidation rate of the food of claim 1, wherein the array of antennas further comprises a radio-frequency waveguide structure.

10. The system for accelerating the oxidation rate of the food of claim 1, wherein the radio-frequency waveguide structure is a ring-shaped structure and comprises a plurality of openings.

11. The system of claim 1, wherein the food is fermented food.

12. The system for accelerating the oxidation rate of the food of claim 11, wherein the food is red wine.

* * * * *